(12) United States Patent
Henrick et al.

(10) Patent No.: US 6,586,624 B1
(45) Date of Patent: Jul. 1, 2003

(54) OXIDATION PROCESS

(75) Inventors: Clive A. Henrick, Palo Alto, CA (US); Randall A. Scheuerman, Santa Clara, CA (US)

(73) Assignee: Syngenta Participations AG, Basel (CH)

( * ) Notice: Subject to any disclaimer, the term of this patent is extended or adjusted under 35 U.S.C. 154(b) by 1434 days.

(21) Appl. No.: 08/570,885

(22) Filed: Dec. 12, 1995

(51) Int. Cl.[7] .................................................. C07C 65/00
(52) U.S. Cl. ........................................ 562/474; 568/774
(58) Field of Search ................................. 568/774, 796, 568/788, 800, 803; 562/474

(56) References Cited

U.S. PATENT DOCUMENTS 3,013,054 A * 12/1961 Richter
4,529,824 A * 7/1985 Mimoun
6,323,377 B1 * 11/2001 Scheuerman \* cited by examiner

*Primary Examiner*—Michael L. Shippen
(74) *Attorney, Agent, or Firm*—William A. Teoli, Jr.; Thomas Hamilton

(57) ABSTRACT

Preparation of 2,5-dichlorophenol by selectively oxidizing 1,4-dichlorobenzene using a peroxo-, hydroperoxo-, superoxo- or alkylperoxo-vanadium species in the presence of an α-hydroxy-, dibasic-, tribasic- or sulfonic acid.

20 Claims, No Drawings

OXIDATION PROCESS

The present invention concerns the selective oxidation of 1,4-dichlorobenzene to 2,5-dichlorophenol.

U.S. Pat. No. 4,529,824 describes in general certain complexes of vanadium, niobium and tantalum and their use in hydroxylating aromatic hydrocarbons either as reactant or catalyst. Additionally, Moiseeva et al. Kinet. Katal 29(4), pp 970–4 (1988) describe oxidation of benzene with vanadium compounds albeit not selectively for phenol (oxidation proceeds at least in part to quinone).

It has now surprisingly been found that oxidation of 1,4-dichlorobenzene to 2,5-dichlorophenol can be effected with improved yield and selectivity when carried out in the presence of certain vanadium derivatives and in the presence of an α-hydroxy-, dibasic-, tribasic- or sulfonic acid.

The present invention therefore provides a process for the preparation of 2,5-dichloro-phenol which comprises selectively oxidizing 1,4-dichlorobenzene using a peroxo-, hydroperoxo-, superoxo- or alkylperoxo-vanadium species in the presence of an acid selected from an α-hydroxy-, dibasic-, tribasic- or sulfonic acid or mixtures thereof.

The reaction may be improved by optional addition of a second acid component selected from formic acid or an alkanoic acid.

The active vanadium species may be prepared by using an oxidation agent. Suitable oxidation agents included organic peroxides such as peroxycarboxylic acids, $RCO_3H$, alkyl hydroperoxides, ROOH, and dialkylperoxides, ROOR, for example peroxyacetic acid, peroxybenzoic acid, peroxytormic acid, t-butyl hydroperoxide, and di-t-butylperoxide and inorganic peroxides such as peroxydisulfuric acid and peroxoborates. The preferred peroxide for use in the invention however, is hydrogen peroxide, especially in aqueous solution. The present process can be carried out at dilutions of 3% to 90% with efficient utilization of $H_2O_2$ and improved yields. However, ca 20–70% e.g. 35–70% aqueous $H_2O_2$ is preferred. The proportions of $H_2O_2$ to 1,4-dichlorobenzene may vary between 0.1 and 5, e.g. between 0.25 and 3. It has been determined that particularly high efficiency may be achieved using approximately equimolar amounts of $H_2O_2$ and 1,4-dichlorobenzene, e.g. ca 0.9 to ca 1.1 molar proportion of $H_2O_2$ per mole of 1,4-dichlorobenzene.

The oxidizing agent is preferably added slowly e.g. dropwise or subsurface to the other reactants with thorough and continuous mixing.

The reaction may be carried out by continuous feed of the reactants or as a batch process.

When hydrogen peroxide is employed addition of small amounts of stabilizers may be of benefit to the reaction in some cases. Examples of such stabilizers include zinc salts, phosphates, pyrophosphates, ascorbic acid, 2,6-di-tert-butyl-4-methylphenol, 5-tert-butyl-4-hydroxy-2-methylphenylsulfide, 8-hydroxy-quinoline or tin compounds such as stannic oxide.

Alternatively use of highly stabilized commercial grades of hydrogen peroxide such as Super D $H_2O_2$ (FMC, Rockland, Me.) or Albone 35CG or 50CG (DuPont Co., Wilmington, Del.) can give superior yield in some conditions.

The peroxo-, hydroperoxo-, superoxo- or alkylperoxo-vanadium species may be and preferably is generated in situ from pure vanadium or from vanadium in the form of a suitable oxide, salt, acetoacetonate or other derivative.

The vanadium may alternatively be used in the form of a polyoxoanion such as decavanadate $[V_{10}O_{28}]^{6-}$ which is generated in situ by employing suitable salts such as e.g. sodium ammonium decavanadate. Keggin type mixed addenda heteropolyanions containing vanadium atoms of the general formula $[XVnM_{12-n}O_{40}]^{(3+m)-}$ where X=P or Si, M=Mo or W, and n=1 to 3, are also effective. (When X=P, m=n; and when X=Si, m=n+1). Other useful Keggin types include molybdo-vanado-tungstophosphoric heteropolyanions of the general formula $[PMo_{3-n}VnW_9O_{40}]^{(3+n)-}$.

Suitable vanadium forms include oxides, acetoacetonates, alkoxy derivatives, sulfates, nitrates, halides, oxyhalides, alkylthiocarbamates or metalates with other cations, (e.g. ammonium metavanadate $NH_4VO_3$ or polyoxovanadate salts such as sodium ammonium decavanadate).

Preferred vanadium forms include oxides, acetoacetonates, alkoxymetal oxides and polyoxoanionic salts such as vanadium (V) oxide ($V_2O_5$) and sodium ammonium decavanadate.

A discussion of peroxo-, hydroperoxo-, superoxo- and alkylperoxo species can be found in Conte et al. in Organic Peroxides Ed. W. Ando, John Wiley & Sons (1992) (pp 559–598).

General descriptions of polyoxoanions and heteropolyanions can be found as follows: Pope, Isopolyanions and Heteropolyanions in Comprehensive Coordination Chemistry (eds. Wilkinson, Gillard & McCleverty), 1987, Ch. 38; Day et al., Science v. 228 n 4699 pp 533–541; Jeannin et al., Pure and Applied Chem. v 59 n 11, pp 1529–1548, 1987; and Pope, Heteropoly and Isopoly Oxometalates, Springer Verlag 1983, Neumann and de la Vega, J. Mol. Catal., v 84, pp 93–108 (1993); Ono, Perpectives in Catalysis (Eds J. M. Thomas and K. I. Zamaraiev), 1992, pp 431–464, Blackwell Scientific Publ., Oxford, the contents of which in this respect are incorporated by reference.

Discussion of hydroperoxide oxidising agents and metal derivatives may also be found in U.S. Pat. Nos. 3,350,422; 3,351,635; 3,360,584; 3,360,585; and 3,662,006.

The vanadium derivatives can be present in amount equivalent to between 0.001 and 100 mol % of metal. Preferably catalytic amounts of 0.05 to 15 mol % are employed.

The vanadium derivative may be recycled and regenerated. For example when an oxide such as vanadium (V) oxide is used the spent catalyst can be heated in air (cf Polish Patent PL 73-165695; C.A. 87.91418) or treated with hydrogen peroxide. Alternatively, the catalyst may be recovered and recycled as is.

The acid component of the process according to the invention is selected from an α-hydroxy-, dibasic-, tribasic- or sulfonic acid. Examples of such acids include oxalic, malonic, 1,2,4-butanetricarboxylic, methanesulfonic, citric, lactic, 3-phenyllactic, 3-chlorolactic, tartaric, glycolic, a phosphoric acid (e.g. phosphoric acid itself, pyrophosphoric acid, polyphosphoric acid and functional equivalents, e.g. phosphorous pentoxide alone or with methanesulfonic acid; cf Eaton et al. J. Org. Chem., v 38, n 23, pp 4071–73(1973)) alkylphosphonic or arylphosphonic acids, e.g. methyl phosphonic, 3-phosphonopropionic, phosphonoacetic, mandelic, glyceric, malic, gluconic, 2,6-pyridinedicarboxylic, sulfuric, o-, m- or p-phthalic and mixtures thereof. In some cases salt forms may be employed e.g. sodium phosphate.

Such acids may be employed where appropriate in various isomeric forms and racemic mixtures thereof. Particularly preferred acids are selected from oxalic, a phosphoric acid and mixtures thereof. The following articles discuss the interaction of vanadium salts with such acids. Caldeira et al.

J. Mol. Struct., v. 174 pp 461–466 (1988); Gil, Pure & Appl. Chem., v 61 n 5, pp 841–848 (1989); Lee et al., Bull Korean Chem. Soc., v 14, n 5, pp 557–561 (1993); Bhattacharjee et al., Can. J. Chem., v 70, pp 2245–8, (1992); Vuletic et al., J.C.S. Dalton Transactions (D.T.), pp 1137–41, 1973; Begin et al., Inorg. Chem., v 14, n 8, pp 1785–90, (1975); Schwendt et al., Z. anorg. allg. Chem., v 466, pp 232–6, (1980); Campbell et al., Inorg. Chim. Acta., v 77, pp L215–6, (1983); Stomberg, Acta Chem. Scand., A40, pp 168–76, (1986); Tracey et al., Inorg. Chem., v 26, pp 629–38 (1987); Tracey et al., Inorg. Chem., v 29, pp 2267–71 (1990); Lee, Bull. Korean Chem. Soc., v 12, n 3, pp 243–4, (1991); Farrell et al., Aust. J. Chem., v 48, pp 763–70 (1995).

The quantity of such acids employed will typically be between 1 and 1000, e.g. 1 to 150 equivalents with respect to the vanadium derivative, for example vanadium (V) oxide. For example when employing phosphoric acid ca 65–75 equivalents with respect to the vanadium catalyst are preferred. These acids are preferably used in highly concentrated form e.g. >80% aqueous or pure anhydrous acid.

The second, optional acid component is selected from formic or an alkanoic acid. Preferred alkanoic acids are lower alkanoic acids containing e.g. 2 to 6 carbon atoms such as acetic, propionic or butyric acid. The preferred acid according to the invention is acetic acid.

The use of co-solvents although not yet essential may also have a beneficial effect on the process according to the invention. Examples of such solvents include aprotic solvents such as chlorinated solvents e.g. 1,2-dichloroethane, dichloromethane, chloroform, nitrated solvents, e.g. nitromethane; nitriles e.g. acetonitrile, propionitrile, benzonitrile; dimethyl-formamide; ketones, e.g. acetone, methylethylketone; alkanes, e.g. hexane; esters e.g. ethylacetate and alcohols e.g. methanol, ethanol, isopropanol; or mixtures thereof.

Reaction temperatures lie between 0 and 150° C. and are preferably in the range of room to elevated (ca 90°) temperature e.g. when employing acetic acid and a vanadium derivative. The reaction is preferably carried out in the substantial absence of water. In certain cases removal of water further increases yield. This is the case for example where the oxidising agent is used in aqueous solution or where water is generated during the reaction. Removal of water can be achieved for example by carrying out the reaction in the presence of a drying agent such as activated molecular sieves (3Å or 4Å), active alumina, silica gel, calcium sulphate, magnesium sulphate, magnesium perchlorate, tetraacetyl diborate or acetic anhydride, etc., or by azeotropic removal of water by distillation with butyl acetate.

In certain cases pH will affect the course of the reaction with lower pH being preferred.

Addition of a salt of the second acid component if present, e. g. dry sodium acetate with acetic acid can increase the yield in certain cases.

Depending on reagents and other conditions carrying out the process in substantial darkness can be an advantage as can inert atmosphere e.g. nitrogen or a noble gas such as argon.

Supply of electrons to the reaction mixture e.g. by the passage of an electrical current through the reaction medium can increase the yield in certain cases.

The reaction mixture may be mono- or multi- e.g. bi-phasic to take advantage of phase transfer effects. [cf Venturello et al., J. Org. Chem., v 48, pp 3831–3 (1983); Bortolini et al., J. Org. Chem., v 50, pp 2688–90 (1985); U.S. Pat. Nos. 4,562,276 and 4,595,671 (1985–6); Bortolini et al., Can. J. Chem., v 64, pp 1189–95 (1986); Venturello et al., J. Org. Chem., v 51, pp 1599–1602, (1986); Bortolini et al., J. Org. Chem., v 51, 2661–3 (1986); Bortolini et al. Studies in Org. Chem., v 33, pp 301–6, (1988), Elsevier, Amsterdam; Venturello et al., J. Org. Chem., v 53, pp 1553–7 (1988); Bianchi et al. J. Mol. Catal. 83 (1993) pp 107–116; Bonchio et al. J. Org. Chem. 54 (1989) pp 4368–4371.]

In a preferred embodiment typically the substrate to be oxidised (1,4-dichlorobenzene) is dissolved in acetic acid and the vanadium derivative (e.g. a high valency vanadium oxide) added with the α-hydroxy-, dibasic-, tribasic- or sulfonic acid component or components followed by the slow addition of the oxidising agent (e.g. aqueous $H_2O_2$) with vigorous mixing. The vanadium derivative may be deposited on a carrier such as silica, alumina, aluminosilicates, zeolites, coals, titanium oxide, quartz, montmorillonite clay, etc. or anchored to a polymer such as polyurea or cross-linked polystyrene or to an ion-exchange resin [cf Linden et al., J. Catal., 43, pp 284–291 (1977); Linden et al., Inorg. Chem., v 16, n 12, pp 3170–3173 (1977); Bhaduri et al., J. Chem. Soc. Dalton Trans 1981 pp 447–451; Yokoyama et al., Chemistry Letters 1983, pp 1703–1706; Bhaduri et al., J. Chem. Soc. Dalton Trans. 1983, pp 415–418; Yokoyama et al., Bul. Chem. Soc. Jpn. 58, pp 3271–3276 (1985); Zhang et al., J. Polymer Sci., v 23,1213–1220 (1985)]; Bhatia et al., Synth. React. Inorg. Met.—Org. Chem., 25 (5), pp 781–796 (1995); Das et al., Tetrahedron Letters, 1995, pp 7909–7912; Choudary et al., J. Chem. Soc., Chem. Commun., 1990, pp 721–722.

The starting material 1,4-dichlorobenzene has the formula

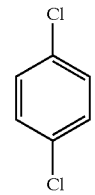

and is a known, commercially available substance.

The desired end product 2,5-dichlorophenol has the formula

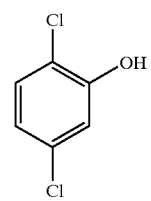

and is useful as an intermediate in the preparation of the commercial herbicide dicamba.

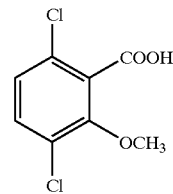

This process involves carboxylation of the 2,5-dichlorophenol to give 2-hydroxy-3,6-dichlorobenzoic acid (a.k.a. 3,6-dichlorosalicylic acid) and methylation of this substrate with subsequent saponification to give dicamba which may be isolated in free acid, salt or ester form (cf e.g. U.S. Pat. No. 3,013,054 for reaction from 2,5-dichlorophenol to dicamba).

The relevant portions of publications and other patent documents cited herein are hereby also incorporated by reference.

The following examples illustrate the invention. Temperatures are in degrees centigrade.

EXAMPLE 1

To a solution of 0.7383 g (5 mmol) of 1,4-dichlorobenzene in 10 ml of acetonitrile is added with stirring 0.68 mL (10 mmol) of 85% aqueous phosphoric acid, and 55 mg (0.3 mmol) of vanadium (V) oxide followed by the gradual infusion of 0.288 mL of 50% aqueous hydrogen peroxide (5 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 2

To a solution of 1.47 g (10 mmol) of 1,4-dichlorobenzene in 10 mL of acetic acid is added with stirring 90 mg (1 mmol) of oxalic acid, 1.5 mL of polyphosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 3

To a solution of 1.47 g (10 mmol) of 1,4-dichlorobenzene in 10 mL of acetic acid is added with stirring 90 mg (1 mmol) of oxalic acid, 0.68 mL (10 mmol) of 85% aqueous phosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This ay be purified e.g. by vacuum distillation (b.p. 70° C. at 2 mm pressure) to give 2,5-dichloro-phenol, m.p. 57–59° C.

EXAMPLE 4

To a solution of 1.47 g (10 mmol) of 1,4-dichlorobenzene in 10 mL of acetic acid is added with stirring 90 mg (1 mmol) of oxalic acid, 0.98 g (10 mmol) of crystalline phosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 5

To a solution of 1.47 g (10 mmol) of 1,4-dichlorobenzene in 10 mL of acetic acid is added with stirring 90 mg (1 mmol) of oxalic acid, 0.89 g (5 mmol) of pyrophosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 6

To a solution of 1.47 g (10 mmol) of 1,4-dichlorobenzene in 10 mL of acetic acid is added with stirring 1.5 mL of polyphosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 7

To a solution of 1.47 g (10 mmol) of 1,4-dichlorobenzene in 10 mL of acetic acid is added with stirring 0.68 mL (10 mmol) of 85% aqueous phosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 8

To a solution of 1.47 g (10 mmol) of 1,4-dichlorobenzene in 10 mL of acetic acid is added with stirring 0.98 g (10 mmol) of crystalline phosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 9

To a solution of 1.47 g (10 mmol) of 1,4-dichlorobenzene in 10 mL of acetic acid is added with stirring 0.89 g (5 mmol) of pyrophosphoric acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 10

To a solution of 1.47 g (10 mmol) of 1,4-dichlorobenzene in 10 mL of acetic acid is added with stirring 90 mg (1 mmol) of oxalic acid, and 55 mg (0.3 mmol) of vanadium(V) oxide followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 11

To a solution of 1.47 g (10 mmol) of 1,4-dichlorobenzene in 10 mL of acetic acid is added with stirring 1.0 mL of polyphosphoric acid, and 81 mg (0.075 mmol) of sodium ammonium decavanadate followed by the gradual infusion of 2 mL of 50% aqueous hydrogen peroxide (30 mmol) over 4 hours. After 24 hours at 20° C. the solid is removed by filtration, and washed with methanol. The combined filtrates are treated dropwise with concentrated aqueous hydrogen bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

We claim:

1. A process for the preparation of 2,5-dichlorophenol which comprises selectively oxidizing 1,4-dichlorobenzene using a peroxo-, hydroperoxo-, superoxo- or alkylperoxo-vanadium species in the presence of an acid selected from an α-hydroxy-, dibasic-, tribasic- or sulfonic acid or mixtures thereof.

2. A process according to claim 1 wherein the metal species is vanadium(V) oxide.

3. A process according to claim 1 wherein the oxidizing agent is a peroxide.

4. A process according to claim 1 wherein the oxidizing agent is a peroxy-carboxylic acid.

5. A process according to claim 1 wherein the oxidizing agent is hydrogen peroxide.

6. A process according to claim 1 where the acid is selected from oxalic, malonic, 1,2,4-butanetricarboxylic, citric, lactic, 3-phenyllactic, 3-chlorolactic, tartaric, glycolic, a phosphoric acid, an alkylphosphonic acid or an arylphosphonic, e.g. methyl phosphonic, 3-phosphonopropionic, phosphonoacetic, mandelic, glyceric, malic, 2,6-pyridinedicarboxylic, gluconic, sulfuric, o-, m- or p-phthalic and mixtures thereof.

7. A process according to claim 1 wherein the acid is selected from oxalic, a phosphoric acid and mixtures thereof.

8. A process according to claim 7 wherein the acid is a phosphoric acid.

9. A process according to claim 1 wherein a second acid component selected from formic or a $C_2$–$C_6$ alkanoic acid is present.

10. A process according to claim 9 wherein the second acid component is acetic acid.

11. A process according to claim 1 which is carried out employing vanadium(V) oxide, a phosphoric acid, acetic acid and an oxidizing agent.

12. A process according to claim 1 wherein the peroxo-, hydroperoxo-, superoxo- or alkylperoxo-metal species is generated in situ from pure vanadium or a suitable vanadium-oxide, salt, acetoacetonate, polyoxo anion or other derivative.

13. A process according to claim 12 wherein the vanadium is added in the form of an oxide, anhydride, acetoacetonate, alkoxymetal derivative, sulfate, nitrate, halide, oxyhalide, alkylthiocarbamate or metalate with other cations.

14. A process according to claim 13 wherein the form is an oxide, acetoacetonate, alkoxymetal oxide, oxychloride or polyoxoanionic salt.

15. A process according to claim 9 wherein a salt of the chosen formic or alkanoic acid is additionally present.

16. A process according to claim 1 wherein aqueous hydrogen peroxide at a dilution of 20–70% is used as the oxidizing agent.

17. A process for preparing dicamba which comprises the steps of, a. selectively oxidizing 1,4-dichlorobenzene using a peroxo-, hydroperoxo-, superoxo-, or alkyleroxo-vanadium species in the presence of an acid selected from the group consisting of an α-hydroxy-, dibasic-, tribasic- or sulfonic acid and mixture thereof, to form 2,5-dichlorophenol, b. carboxylating the 2,5-dichlorophenol to give 2-hydroxy-3,6-dichlorobenzoic acid, c. methylating the 2-hydroxy-3,6-dichlorobenzoic acid and saponifying the product to give dicamba which may be isolated in free acid or salt or ester form.

18. A process according to claim 17 wherein the metal species is vanadium(V) oxide and the oxidizing agent is hydrogen peroxide.

19. A process according to claim 17 which is carried out employing vanadium(V) oxide, a phosphoric acid, acetic acid and an oxidizing agent.

20. A process for the preparation of 2,5-dichlorophenol which comprises selectively oxidizing 1,4-dichlorobenzene using a peroxo-, hydroperoxo-, superoxo- or alkylperoxo vanadium species in the presence of an acid selected from the group consisting of phosphoric, alkylphosphonic and arylphosphonic acids.

* * * * *